(12) United States Patent
Sokolova et al.

(10) Patent No.: US 8,043,805 B2
(45) Date of Patent: Oct. 25, 2011

(54) DETECTION OF HIGH GRADE DYSPLASIA IN CERVICAL CELLS

(75) Inventors: Irina A. Sokolova, Villa Park, IL (US); Steven A. Seelig, Elmhurst, IL (US); Larry E. Morrison, Glen Ellyn, IL (US); Walter King, Wheaton, IL (US); Alicia Algeciras-Schimnich, Naperville, IL (US)

(73) Assignee: Vysis, Inc., Downers Grove, IL (US)

( * ) Notice: Subject to any disclaimer, the term of this patent is extended or adjusted under 35 U.S.C. 154(b) by 33 days.

(21) Appl. No.: 12/422,859

(22) Filed: Apr. 13, 2009

(65) Prior Publication Data

US 2009/0269768 A1 Oct. 29, 2009

Related U.S. Application Data

(63) Continuation of application No. 10/857,859, filed on Jun. 2, 2004, now Pat. No. 7,517,645, which is a continuation-in-part of application No. 10/457,639, filed on Jun. 9, 2003, now abandoned.

(51) Int. Cl.
*C12Q 1/68* (2006.01)
*C12P 19/34* (2006.01)
*C12M 1/34* (2006.01)
*C07H 21/02* (2006.01)
*C07H 21/04* (2006.01)

(52) U.S. Cl. ....... 435/6; 435/9.12; 435/287.1; 536/23.1; 536/24.3

(58) Field of Classification Search .......................... None
See application file for complete search history.

(56) References Cited

U.S. PATENT DOCUMENTS

| | | | |
|---|---|---|---|
| 5,491,224 A | 2/1996 | Bittner et al. | |
| 5,658,730 A | 8/1997 | McGill et al. | |
| 5,756,696 A | 5/1998 | Gray et al. | |
| 5,776,688 A | 7/1998 | Bittner et al. | |
| 5,789,161 A | 8/1998 | Morrison et al. | |
| 5,919,624 A | 7/1999 | Ried et al. | |
| 6,174,681 B1 | 1/2001 | Halling et al. | |
| 6,376,188 B1 | 4/2002 | Halling et al. | |
| 7,517,645 B2 * | 4/2009 | Sokolova et al. | 435/6 |
| 2003/0087248 A1 | 5/2003 | Morrison et al. | |

FOREIGN PATENT DOCUMENTS

| | | |
|---|---|---|
| WO | 24760 | 5/2000 |
| WO | 53536 | 7/2001 |

OTHER PUBLICATIONS

Kirchhoff M. et al. Genes, Chromosomes & Cancer (1999) vol. 24, pp. 144-150.*
Aubele M. et al. Cancer Cytopathology (1998) vol. 84, No. 6, pp. 375-379.*
Golijow C.D. et al. Int J Gynecol Cancer (2001) vol. 11, p. 462-465.*
Morrison, L. et.al., Molecular Cytogenetics: Protocols and Applications, Chap. 2, "Labeling Fluorescence In Situ Hybridization Probes for Genomic Targets," Humana Press, (2002): 21-40.
Lazo, P. A., Brit. J. Cancer, 80, (12), (1999): 2008-2018.
Hopman, et al., J. of Pathology, 202, (2004): 23-33.
Nath, J. and Kirby L. Johnson, Biotechnic & Histochem. 73, (1), (1998): 6-22.
Wheeless, et al., Cytometry, 17, (1994): 319-327.
Zakut, H., et al, In vivo gene amplification in non-cancerous cells: cholinesterase genes and oncogenes amplify in thrombocytopenia associated with lupus erythematosus, Mutat. Res., 276, (3), (1992): 275-384.
Schraml, P. et al., 'Tissue microarrays for gene amplification surveys in many different tumor types.' Clin. Cancer Res., 5, (1999): 1966-1975.
LSI-CMYC description and map, available online from www.vysis.com, pp. 1-2. (Jun. 4, 2009).
Bork, P. et al., 'Convergent evolution of similar enzymatic function on different protein folds: The hexokinase, ribokinase, and galactokinase families of sugar kinases, Protein Sci., 2, (1993): 31-40.
Juppner H., 'Functional properties of the PTH/PTHrP receptor.' Bone 17, 2 (Suppl.), (1995): 39S-42S.
Thisted, Ronald, A., 'What is a P-Value', available online from www.stat.uchicago.edu/thisted, pp. 1-6. (May 25, 1998).
Zhu, C-Q, et al., 'Amplification of telomerase (hTERT) gene is a poor prognostic marker in non-small-cell lung cancer. Br J. of Cancer, 94,10, (2006): 1452-1459.
Mian, C. et al., 'Fluorescence in situ hybridization in cervical smears: detection of numerical aberrations of chromosomes 7, 3, and X and relationship of HPV infection.' Gynecol. Oncol., 75, 1, (1999): 41-46.
Sano, T. et al., 'Immunohistochemical overexpression of p16 protein associated with intact retinoblastoma protein expression in cervical cancer and cervical intraepithelial neoplasia.' Pathol Int. 48, (8), (1998): 580-585.
Brink, A. et al., 'Simultaneous mapping of human papillomavirus integration sites and molecular karyotyping in short-term cultures of cervical carcinomas by using 49-color combined binary ratio labeling fluorescence in situ hybridization. Cancer Genet. and Cytogenet., 134, (2), (2002): 145-150.

(Continued)

*Primary Examiner* — Stephen Kapushoc
(74) *Attorney, Agent, or Firm* — Pierce Atwood, LLP; Kevin M. Farrell; David J. Wilson

(57) ABSTRACT

Methods of using probes and probe sets for the detection of high grade dysplasia and carcinoma in cervical cells are described. Methods of the invention include hybridizing one or more chromosomal probes to a biological sample obtained from a subject and detecting the hybridization pattern of the chromosomal probes to the sample to determine whether the subject has high grade dysplasia or carcinoma. Methods of the invention also include preliminary screening the cells for a marker associated with a risk for cancer, and preferably involves screening for HPV infected cells by in situ hybridization using an HPV probe mixture.

23 Claims, No Drawings

OTHER PUBLICATIONS

Rihakova, P. et al., 'DNA ploidy correlates with grade, proliferation and clinical outcome but not with presence of human oncogenic HPVs or expression of Bcl-2 in preneoplastic and neoplastic lesions of the uterine cervix.' Neoplasma. 48, 4, (2004): 274-277.

Hyott, M. J. 'Cervial Dysplasia and Cancer' 1998, from www.thebody.com/cria/spring98/dysplasia.html. 1-5.

Heselmeyer, K. et al., 'Gain of chromosome 3q defines the transition from severe dysplasia to invasive carcinoma of the uterine cervix.' Proc Natl Acad Sci. U.S.A 93, 1, (1996): 479-484.

Heselmeyer-Haddad, K. et al., 'Detection of genomic amplification of the human telomerase gene (TERC) in cytologic specimens as a genetic test for the diagnosis of cervical dysplasia.' Am. J. Pathol. 163, 4, (2003): 1405-1416.

Golijow C. D, et al., 'c-myc gene amplification detected in preinvasive intraepithelial cervical lesions.' Int J Gynecol. Cancer 11, 6, (2001): 462-5.

Zhang, A. et al., Genetic Alterations in Cervical Carcinomas: Frequent Low-Level Amplifications of Oncogenes Are Associated with Human Papillomavirus Infection, Int. J. Cancer 101, (2002): 427-433.

Bubenddorf, L. et al., Survey of Gene Amplifications during Prostate Cancer Progression by High-Throughput Fluorescence in Situ Hybridization on Tissue Microarrays, Cancer Research 59, (1999): 803-806.

Woenckhaus, J. et al., Genomic gain of PIK3CA and increased expression of p110alpha are associated with progression of dysplasia into invasive squamous cell carcinoma, J. Path.198, (2002): 335-342.

Mark, H. F. L. et al., Assessment of Chromosome 8 Copy No. in Cervical Cancer by Fluorescent in situ Hybridization, Experimental and Molecular Pathology, 66, (1999): 157-162.

Heselmeyer, K. et al., Advanced-Stage Cervical Carcinomas Are Defined by a Recurrent Pattern of Chromosomal Aberrations Revealing High Genetic Instability and a Consistent Gain of Chromosome Arm 3q, Genes, Chromosomes & Cancer 19 (1997): 233-240.

Wiegant, J. et al., Differentially Painting Human Chromosome Arms with Combined Binary Ratio-labeling Fluorescence in situ Hybridization, Genome Research 10, (2000): 861-865.

* cited by examiner

DETECTION OF HIGH GRADE DYSPLASIA IN CERVICAL CELLS

This application is a Continuation application citing priority to U.S. patent application Ser. No. 10/857,859, filed on Jun. 2, 2004, now U.S. Pat. No. 7,517,645, which is a Continuation-in-part of U.S. patent application Ser. No. 10/457,639, filed on Jun. 9, 2003, now abandoned.

BACKGROUND OF THE INVENTION

Cervical cancer remains one of the most common cancer types affecting women worldwide. The biological pathway to cervical carcinoma begins with normal intraepithelial cells, and develops through low and then high grade dysplasia before malignancy obtains. Cytologists mark the passage to malignancy as progression from normal epithelial cells to atypical squamous cells of undetermined significance (AS-CUS) to Low Grade squamous intraepithelial lesions (LSIL) and then high grade squamous intraepithelial lesions (HSIL) before carcinoma in situ and finally malignancy result. Histologists mark the progression from normal cells to various grades of cervical intraepithelial neoplasia (CIN I, II and III), then to carcinoma in situ and finally malignancy. CIN I is considered low grade dysplasia comparable to LSIL. CIN II and III are considered high grade dysplasia comparable to HSIL.

The current standard of care includes regular cytologic testing with a Papanicolau (Pap) smear to identify abnormalities as indicating dysplasia or carcinoma in patient cells. When high grade dysplasia is detected and confirmed by histological examination, the transformation zone of the patient's cervix is removed immediately by loop excision or cone biopsy. More radical procedures are required when carcinoma is detected. At the same time, however, the progression from normal to malignancy is not strict and the presence of low grade dysplasia does not necessarily indicate that the patient will progress to high grade dysplasia or malignancy. Significantly, the negative predictive value of cytologic methods (e.g., Pap smears) for detecting high grade dysplasia is poor. Thus, low grade dysplasia may be misdiagnosed as high-grade, thereby subjecting the patient to unwarranted treatment and high grade dysplasia may be misdiagnosed as low grade dysplasia, thereby delaying appropriate treatment. Accordingly, there is a need for a diagnostic method that will accurately distinguish between low and high grade dysplasia.

Patient specimens typically comprise many thousands of cells for evaluation. Diagnosis based on evaluation of individual cells can be enormously time consuming and tedious for technicians to perform due to the large number of cells that are required for evaluation. Thus, there is a need for a means to simplify a cell evaluation method.

Others have noted that genetic abnormalities (e.g., changes in chromosome regions or changes in ploidy levels) accompany the progression from normal cells to cervical malignancy. See, e.g., U.S. Pat. No. 5,919,624 to Ried, et al. Ried et al. noted that chromosomal abnormalities can be used to classify the progression of dysplastic cervical cells in late stages, e.g., from noninvasive cervical to invasive cervical carcinoma. Still others have demonstrated that cervical cancer is associated with infection by certain human papilloma viruses (HPV) types, particularly HPV types 16, 18, 31, 33, 35 and 42. See, e.g., Lazo, Brit. J. Cancer, (1999) 80(12), 2008-2018. Additionally, many cell cycle proteins such as p16 and Cyclin E and cell proliferation markers such as the proteins Ki67 and PCNA are also known to be highly active in neoplastic cells. Thus, cells containing abnormal amounts of these markers have been suggested as good candidates for cells that may progress to malignancy.

PCT application WO 0024760 describes methods and reagents for detecting HPV DNA in Pap smears using in situ hybridization and brightfield microscopy. The probe consists of full length DNA probes of HPV-16, -18, -31, -33, -35, and -51. The patent claims that this probe mix detects other high-risk BPV types but not low-risk HPV. The ability of the disclosed HPV probe mixture to avoid hybridization to low-risk BPV types is achieved by modulation of the quantities of each HPV DNA probe included on the probe mix. The BPV probes disclosed are different than those described herein. In addition, the assays of the invention modulate probe cross-hybridization by lowering the stringency of the hybridization conditions while keeping the probe concentrations constant for all types. This application also does not combine HPV probe with use of chromosomal probes to detect chromosome abnormalities in the HPV infected cells.

Hopman et al. (J of Pathology 2004; 202:23-33) analyzed HPV status and chromosomal aberrations in cervical biopsies sections by FISH. This work used only probes for HPV-16 and BPV-18 and genomic probes for chromosome 1 (1q12), 17, and X. In contrast to the inventive assay that simultaneously detect HPV and chromosomal gains in the same cells, Hopman et al.'s detection of HPV positive cells and chromosomal aberrations was performed in parallel tissue sections.

To date Applicants are not aware of any publication that has demonstrated that any chromosomal abnormality with or without the presence of another marker can be used to distinguish low from high grade dysplasia or has combined such a diagnostic method with the known association of HPV and cervical cancer.

SUMMARY OF THE INVENTION

The invention is based on the discovery that certain chromosomal abnormalities can be used to selectively detect high grade cervical intraepithelial neoplasia (CIN II and CIN III) and malignant carcinoma in cervical biopsy and Pap smear specimens without detecting low grade cervical intraepithelial neoplasia. The method can detect high grade cervical intraepithelial neoplasia (CIN II and CIN III) and malignant carcinoma at high sensitivity and specificity levels, i.e. about 95% each. The invention is based on the use of in situ hybridization technology where labeled nucleic acid probes are allowed to hybridize to cervical samples. Preferably, fluorescent in situ hybridization (FISH) is used and the nucleic acid probes are DNA probes that are fluorescently labeled. The hybridization results are then correlated with a clinical diagnosis of high grade cervical intraepithelial neoplasia (CIN II and CIN III) and malignant carcinoma.

The method of the invention utilizes a set of one or more probes demonstrating a vector value for discriminating between CIN I and CIN II of about 60 or less, wherein the vector value is calculated by Vector=$[(100\text{-specificity})^2+(100\text{-sensitivity})^2]^{1/2}$. Preferred probes for use in the method are probes to the genetic loci 3q26, 8q24, 20q13, Xp22 and 3p21, and probes that enumerate chromosomes 3 and 15. Multiple probe sets comprising two, three or more probes can be used in the method of the invention. Preferred multiprobe sets comprise probes to the genetic loci 8q24 and 3q26; 3q26, 8q24, Xp22, and chromosome 15; 8q24, 20q13, Xp22 and chromosome 15; and the genetic loci 3p21, 3 p14, 3q26 and chromosome 3. Probes useful in the invention can be incorporated into kits packaged, for example, with other reagents useful in carrying out the methods of the invention. Such kits can comprise one or more probes useful with the invention.

Probes can be selected using the steps of: (a) providing a first plurality of chromosomal probes (by plurality is meant one or more probes); (b) determining the ability of each of the first plurality of probes to distinguish high (CIN II, CIN III and carcinoma) from low (CIN I) grade dysplasia in a cervical specimen; and (c) selecting the probe or probes within the first plurality of probes that distinguish high from low grade dysplasia to yield a second plurality of probes, wherein the second plurality of probes identifies the high grade dysplasia specimens as compared to low grade specimens at a vector value of less than about 60. Preferred probes can be selected by additionally: (d) determining the ability of a combination of probes selected from the second plurality of probes to distinguish the high grade from low grade specimens; and (e) selecting a combination of probes that identifies the high grade specimen as compared to the low grade specimen with a vector value of less than about 40. More preferred embodiments can be selected based on lower vector values (e.g., a vector value of less than about 30).

The biological sample used with the invention can contain a cervical biopsy specimen or a cervical smear such as a Pap smear or a ThinPrep® sample prepared by the method of Cytyc Corp., Boxborough, Mass. The probes used with the invention comprise detectably labeled nucleic acid-based probes, such as deoxyribonucleic acid (DNA) probes or protein nucleic acid (PNA) probes, which are desiped/selected to hybridize to the specific designed chromosomal target. Fluorescent labels such as are used in fluorescent in situ hybridization are preferred but other detectable labels commonly used in hybridization techniques, e.g., enzymatic, chromogenic and isotopic labels, can also be used.

In another aspect of the invention, the detection of the genetic abnormalities is facilitated by adoption of a preliminary cell screening technique whereby cervical cells are screened first for the presence of a suitable associated marker, for example, such as the presence of infection by EPV, e.g., high risk HPV, or abnormal amounts of cell cycle proteins such as p16 and Cyclin E or cell proliferation markers such as Ki67 and PCNA. Such screening can be used to identify more suspicious cells for closer examination and may allow the time required for specimen evaluation to be reduced by as much as 5-10 fold. After the suspicious cells are identified, these suspicious cells are then examined for the presence of chromosomal abnormalities. The presence of chromosomal abnormalities identified by use of the probes of the invention in cells also showing markers of potential malignancy, such as HPV infection, identifies higher grade CIN or malignancy. Such initial screening techniques are amenable to automation, enabling greater simplicity and speed in specimen evaluation.

A preferred assay comprises the simultaneous detection of HPV infection and chromosomal gains by fluorescence in situ hybridization in individual cells on cervical cytological specimens to identify higher grade disease. This preferred assay comprises a method for screening for high grade dysplasia in a subject, the method comprising: (a) obtaining a biological sample from the subject; (b) contacting the sample with a set of one or more chromosomal probes and with a mixture of HPV probes under conditions sufficient to enable hybridization of the probes to chromosomes in the sample if any and sufficient to enable detection of HPV infected cells present in the sample if any; (c) detecting the presence of HPV infected cells in the sample; and (d) determining hybridization pattern of the chromosomal probes in the BPV infected cells in the sample to determine whether the subject has high grade dysplasia. Detection of HPV is preferably done with a mixture of six HPV full-length genomic probes (HPV-16, BPV-18, HPV-30, HPV-45, HPV-51, and HPV-58) under low stringency hybridization conditions. Use of this mixture under low stringency conditions will detect the following HPV types: HPV-16, HPV-18, HPV-31, HPV-33, HPV-35, HPV-39, HPV-45, HPV-51, HPV-52, BPV-56, HPV-58, BPV-59, HPV-26, HPV-53, and HPV-66. Preferably, the six HPV probes in the mixture are labeled so that the probes are detected using a fluorescence labeled tyramide signal amplification-system. Detection of chromosomal gains preferably is done with three directly labeled probes, each labeled in a fluorescent color distinct from the others and from the HPV cocktail detection color: to chromosomal locus 8q24 and 3q26 and to the centromere of chromosome 8. The determination of a hybridization pattern indicative of the presence of chromosomal abnormalities in cells infected with high-risk HPV correlates with high-grade dysplasia.

DETAILED DESCRIPTION OF THE INVENTION

The invention includes (i) methods of using probes and (ii) probe sets for the detection of high grade dysplasia and carcinoma in cervical cells. The methods and probe sets allow for the early detection of high grade dysplasia in biological samples, such as a cervical biopsies and smears.

Chromosomal Probes

Suitable probes for use in the in situ hybridization methods utilized with the invention fall into two broad groups: chromosome enumeration probes, i.e., probes that hybridize to a chromosomal region, usually a repeat sequence region, and indicate the presence or absence of an entire chromosome, and locus specific probes, i.e., probes that hybridize to a specific locus on a chromosome and detect the presence or absence of a specific locus. Chromosome arm probes, i.e., probes that hybridize to a chromosomal region and indicate the presence or absence of an arm of a specific chromosome, may also be useful. Chromosomal probes and combinations thereof are chosen for sensitivity and/or specificity when used in methods of the invention. Probe sets can comprise any number of probes, e.g., 1, 2, 3, 4 or more probes. The number of probes useful with the invention is limited only by the user's ability to detect the probes on an individual basis.

As is well known in the art, a chromosome enumeration probe can hybridize to a repetitive sequence, located either near or removed from a centromere, or can hybridize to a unique sequence located at any position on a chromosome. For example, a chromosome enumeration probe can hybridize with repetitive DNA associated with the centromere of a chromosome. Centromeres of primate chromosomes contain a complex family of long tandem repeats of DNA comprised of a monomer repeat length of about 171 base pairs, that are referred to as alpha-satellite DNA. Non-limiting examples of chromosome enumeration probes include probes to chromosomes 1, 6, 7, 8, 9, 10, 11, 12, 15, 16, 17, 18 and X. Examples of several specific chromosome enumeration probes are described in Example 1.

A locus specific probe hybridizes to a specific, non-repetitive locus on a chromosome. Non-limiting examples of locus specific probes include probes to the following loci: 3q26, 8q24, 20q13, Xp22 and 3p21. Some of these loci comprise genes, e.g., oncogenes and tumor suppressor genes that are altered in some forms of cervical cancer. Thus, probes that target these genes, either exons, introns, or regulatory chromosomal sequences of the genes, can be used in the detection methods described herein. Examples of target genes include: TERC (3q26); MYC (8q24); STK6 (20q13.2-13.3) and MLH (3p21-p23). Additional examples are identified in Example 1.

Probes that hybridize with centromeric DNA and specific chromosomal loci are available commercially from Vysis, Inc. (Downers Grove, Ill.) and Molecular Probes, Inc. (Eugene, Oreg.). Alternatively, probes can be made non-commercially using well known techniques. Sources of DNA for use in constructing DNA probes include genomic DNA, cloned DNA sequences such as bacterial artificial chromosomes (BAC), somatic cell hybrids that contain one or a part of a human chromosome along with the normal chromosome complement of the host, and chromosomes purified by flow cytometry or microdissection. The region of interest can be isolated through cloning or by site-specific amplification via the polymerase chain reaction PCR). See, for example, Nath, et al., Biotechnic Histochem, 1998, 73 (1): 6-22; Wheeless, et al., Cytometry, 1994, 17:319-327; and U.S. Pat. No. 5,491,224. Synthesized oligomeric DNA or PNA probes can also be used.

The size of the chromosomal region detected by the probes used in the invention can vary, for example, from the alpha satellite 171 base pair probe sequence noted above to a large segment of 150,000 bases. For locus-specific probes, that are directly labeled, it is preferred to use probes of at least 100,000 bases in complexity, and to use unlabeled blocking nucleic acid, as disclosed in U.S. Pat. No. 5,756,696, herein incorporated by reference, to avoid non-specific binding of the probe. It is also possible to use unlabeled, synthesized oligomeric nucleic acid or protein nucleic acid as the blocking nucleic acid. For targeting a particular gene locus, it is preferred that the probes span the entire genomic coding locus of the gene.

Chromosomal probes can contain any detection moiety that facilitates the detection of the probe when hybridized to a chromosome. Effective detection moieties include both direct and indirect labels as described below.

Chromosomal probes can be directly labeled with a detectable label. Examples of detectable labels include fluorophores, i.e., organic molecules that fluoresce after absorbing light, and radioactive isotopes, e.g., $^{32}P$, and $^{3}H$. Fluorophores can be directly labeled following covalent attachment to a nucleotide by incorporating the labeled nucleotide into the probe with standard techniques such as nick translation, random priming, and PCR labeling. Alternatively, deoxycytidine nucleotides within the probe can be transaminated with a linker. The fluoropore can then be covalently attached to the transaminated deoxycytidine nucleotides. See, e.g., U.S. Pat. No. 5,491,224 to Bittner, et al., which is incorporated herein by reference. Useful probe labeling techniques are described in Molecular Cytogenetics: Protocols and Applications, Y.-S. Fan, Ed., Chap. 2, "Labeling Fluorescence In Situ Hybridization Probes for Genomic Targets", L. Morrison et. al., p. 21-40, Humana Press, © 2002 (hereafter cited as "Morrison-2002"), incorporated herein by reference.

Examples of fluorophores that can be used in the methods described herein are: 7-amino-4-methylcoumarin-3-acetic acid (AMCA), Texas Red™ Molecular Probes, Inc., Eugene, Oreg.); 5-(and -6)-carboxy-X-rhodamine, lissamine rhodamine B, 5-(and -6)-carboxyfluorescein; fluorescein-5-isothiocyanate (FITC); 7-diethylaminocoumarin-3-carboxylic acid, tetramethyl-rhodamine-5-(and -6)-isothiocyanate; 5-(and -6)-carboxytetramethylrhodamine; 7-hydroxy-coumarin-3-carboxylic acid; 6-[fluorescein 5-(and -6)-carboxamido]hexanoic acid; N-(4,4-difluoro-5,7-dimethyl-4-bora-3a, 4a diaza-3-indacenepropionic acid; eosin-5-isothiocyanate; erythrosine-5-isothiocyanate; 5-(and -6)-carboxyrhodamine 6G; and Cascades blue aectylazide (Molecular Probes, Inc., Eugene, Oreg.).

When multiple probes are used, fluorophores of different colors can be chosen such that each chromosomal probe in the set can be distinctly visualized. Preferably the probe panel of the invention will comprise four separate probes, each labeled with a separate fluorophore. Use of four probes is preferred because Applicants believe this provides the best balance between clinical sensitivity (sensitivity can increase with added probes) and imaging/detection complexity (complexity can increase with added probes). It is also within the scope of the invention to use multiple panels sequentially on the same sample: in this embodiment, after the first panel is hybridized, the results are imaged digitally, the sample is destained and then is hybridized with a second panel.

Probes can be viewed with a fluorescence microscope and an appropriate filter for each fluorophore, or by using dual or triple band-pass filter sets to observe multiple fluorophores. See, e.g., U.S. Pat. No. 5,776,688 to Bittner, et al., which is incorporated herein by reference. Any suitable microscopic imaging method can be used to visualize the hybridized probes, including automated digital imaging systems, such as those available from MetaSystems or Applied Imaging. Alternatively, techniques such as flow cytometry can be used to examine the hybridization pattern of the chromosomal probes.

Probes can also be labeled indirectly, e.g., with biotin or digoxygenin by means well known in the art. However, secondary detection molecules or further processing are then required to visualize the labeled probes. For example, a probe labeled with biotin can be detected by avidin conjugated to a detectable marker, e.g., a fluorophore. Additionally, avidin can be conjugated to an enzymatic marker such as alkaline phosphatase or horseradish peroxidase. Such enzymatic markers can be detected in standard colorimetric reactions using a substrate for the enzyme. Substrates for alkaline phosphatase include 5-bromo-4-chloro-3-indolylphosphate and nitro blue tetrazolium. Diaminobenzoate can be used as a substrate for horseradish peroxidase. Fluorescence detection of a hybridized biotin or other indirect labeled probe can be achieved by use of the commercially available tyramide amplification system.

Detection of HPV can be done using one or more probes comprising the entire genomic sequence, of an BPV type or a partial genomic sequence, such as a mixture of whole genomic probes to HPV types 16 and 18. The HPV probe mixture used should be sufficient to identify the presence of the major high risk types, including HPV-16, HPV-18, BPV-31, HPV-33, HPV-35, HPV-39, HPV-45, HPV-51, HPV-52, BPV-56, HPV-58, BPV-59, HPV-26, HPV-53, and HPV-66. A preferred mixture comprises six full-length PV genomic probes (HPV-16, HPV-18, HPV-30, HPV-45, HPV-51, and HPV-58) which is used under low stringency hybridization conditions. These six probes were selected based on sequence homology analysis with other high-risk HPV types. Based on sequence homology and on the assumption that HPV types with 50% or higher homology to these six HPV types will show cross-hybridization, use of this preferred mixture under low stringency conditions will detect the following HPV types: HPV-16, HPV-18, HPV-31, HPV-33, HPV-35, HPV-39, HPV-45, HPV-51, HPV-52, HPV-56, HPV-58, HPV-59, BPV-26, HPV-53, and HPV-66. In this preferred mixture, the concentrations of each of the six HPV probes is maintained at approximately equal amounts, which is preferably less than a 5 percent difference in the individual probe amounts by weight. Preferably, the six HPV probes in the mixture are labeled so that the probes are detected using a fluorescence labeled tyramide signal amplification system.

The probes and probe sets useful with the methods of the invention can be packaged with other reagents into kits to be used in carrying out the methods of the invention. Useful kits can comprise one or more probes from the group of probes to the genetic loci 3q26, 8q24, 20q13, Xp22 and 3p21, and probes that enumerate chromosomes 3 and 15. A preferred kit of the invention comprises four probes: (i) a biotin labeled mixture of six HPV probes (for HPV types 16, 18, 30, 45, 51 and 58); (ii) a chromosomal probe to TERC gene locus at 3q26; (iii) a chromosomal probe to the cmyc gene locus at 8q24; and (iv) a chromosomal probe to the centromere of chromosome 8.

Determining the Presence of High Grade Dysplasia

Pre-Selection of Cells

Cell samples can be evaluated preliminarily by a variety of methods and using a variety of criteria. The probes and methods described herein are not limited to usage with a particular screening methodology. One example is the "scanning method" wherein the observer scans hundreds to thousands of cells for cytologic abnormalities, e.g., as viewed with a DAPI filter. The number of cells assessed will depend on the cellularity of the specimen, which varies from patient to patient. Cytologic abnormalities commonly but not invariably associated with dysplastic and neoplastic cells include nuclear enlargement, nuclear irregularity, and abnormal DAPI staining (frequently mottled and lighter in color). In the scanning step, the observer preferably focuses the evaluation of the cells for chromosomal abnormalities (as demonstrated by FISH) to those cells that also exhibit cytological abnormalities. In addition, a proportion of the cells that do not have obvious cytologic abnormalities can be evaluated since chromosomal abnormalities also occur in the absence of cytologic abnormalities. This scanning method is described in further detail in U.S. Pat. No. 6,174,681 to Halling, et al., which is incorporated herein by reference.

More preferably, the observer can scan the cells for a marker associated with cancer. For example, the cells can be scanned for the presence of an associated marker such as the presence of BPV or high risk HPV (e.g., one or more of PV types 16, 18, 31, 33, 35 or 45). Additionally, cells with abnormal amounts of the cell cycle proteins p16 and Cyclin E or the proliferation markers Ki67 and PCNA are likely to be suspicious and good candidates for closer examination. Cells can be scanned for the presence of these markers using well know methods. Cell scanning is generally amenable to automation. Automated scanning permits increased efficiency by permitting assays to be performed more rapidly and eliminating much of the tedium present in manual scanning.

Preparation of Samples

The presence or absence of high grade dysplasia and carcinoma can be determined by identifying chromosomal aberration in the cells. This can be accomplished by in situ hybridization. In general, in situ hybridization includes the steps of fixing a biological sample, hybridizing a chromosomal probe to target DNA contained within the fixed sample, washing to remove non-specifically bound probe, and detecting the hybridized probe. The in situ hybridization can also be carried out with the specimen cells in liquid suspension, followed by detection by flow cytometry.

Abnormal cells are characterized by abnormal numbers of chromosomes within the cells and/or structural alterations within the cells' chromosomes. Structural alterations can include gains or losses (e.g., hemizygous or homozygous loss) of a specific chromosomal region, such as a locus or centromeric region as indicated in Example 1. Positive test indicators can be developed accordingly. For example, a cell having one or more chromosomal gains, i.e., three or more copies of any given chromosome, can be considered to test positive in the methods described herein. Cells exhibiting monosomy or nullisomy may also be considered test positive under certain circumstances.

A biological sample is a sample that contains cells or cellular material, e.g., cells or material derived from the uterine cervix of the uterus. Examples of cervical specimens include cervical biopsies, smears, scrapes and the like. Typically, cells are harvested from a biological sample and prepared using techniques well known in the art. Numerous methods are available for collecting cervical cells for evaluation. For example, cells from the ectocervix and endocervix/transformation zone are collected using well-known devices such as endocervical brushes (or "brooms") or wooden and plastic spatulas. Conventional smears are prepared by spreading cells evenly and thinly onto a glass slide. The slide is then fixed rapidly by immersion into 95% ethanol or spraying with a commercial fixative according to manufacturer instructions.

For the ThinPrep® collection method (Cytyc Corp., Boxborough, Mass.), cells are transferred from the cervix into the fixative PreservCyt®. This allows cells to be preserved until ready for further processing. Cells are then gently dispersed, randomized and collected onto a TransCyt® membrane filter by drawing the sample across the filter with a vacuum until an optimal number of cells is deposited into the filter. The cells can be further processed as desirable. In another method, the cells collected into PreservCyt® or other fixative solution can be further washed by centrifuging, removing the supernatant and resuspending in Carnoys solution (3:1 Methanol:Acetic acid), repeating (e.g., three times) as desired. Cells are then transferred to a glass slide by dropping a small aliquot of cell suspension directly onto the slide. Slides are typically dried overnight.

Detection of Chromosomal Abnormalities

Gain or loss of chromosomes or chromosomal regions within a cell is assessed by examining the hybridization pattern of the chromosomal probe or set of chromosomal probes (e.g., the number of signals for each probe) in the cell, and recording the number of signals. Test samples can comprise any number of cells that is sufficient for a clinical diagnosis, and typically contain at least about 100 cells. In a typical assay, the hybridization pattern is assessed in about 25-5,000 cells. Test samples are typically considered "test positive" when found to contain a plurality of chromosomal abnormalities, e.g., cells present gains or losses of one or more chromosomes, loci or chromosomal arms as described herein. Criteria for "test positive" can include testing positive with one, two, three, four or more probes. Testing positive with one probe is a typical test criterion; testing positive with two probes is more preferred, and with four is most preferred. In addition, when multiple probes are used test positive can include detection of abnormal hybridization patterns with a subset of probes, e.g., a combination of gains or losses of a subset of the probes, e.g., two or three probes of a full set of four probes. Hybridization patterns can be assessed in sequence for subsets of probes. For example, the pattern of an initial subset of probes (e.g., probes to the 3q26 and 8q24 loci) can be assessed and, if a positive result is indicated from the subset of probes the test can be taken as positive overall. However, if the initial result is not positive, the pattern for an additional subset of probes (e.g., probes to the Xp22 locus and chromosome 15) can be assessed to complete the test. If the combined result for all probes indicates a positive test result, the test can be taken as positive overall.

The number of cells identified with chromosomal abnormalities and used to classify a particular sample as positive, in general will vary with the number of cells in the sample. As low as one cell may be sufficient to classify a sample as positive. It is preferred to identify at least 30 cells as positive, more preferred to identify at least 10 cells, and most preferred to identify at least 5 cells as positive. The number of cells used for a positive classification is also known as the cut-off value, which is discussed further below.

Screening and Monitoring Patients for High Grade Dysplasia and Cervical Carcinoma The methods described herein can be used to screen women for high grade dysplasia as a predecessor to cervical carcinoma. For example, women at risk for cervical cancer, e.g., women with abnormal PAP smear, women who are infected with a HPV, e.g., high risk HPV, or women that show abnormal amounts of cell cycle proteins such as p16 and Cyclin E or cell proliferation proteins such as Ki67 and PCNA can be regularly screened with the goal of early detection of progression to high grade dysplasia. For example, general probes and methods to detect infection by HPV in a sample can be used, such as, for example, a whole genomic HPV probe. Type specific probes can also be developed to detect infection by specific HPV types such as one or more of the high risk HPV types HPV 16, 18, 31, 33, 35, 45, 51, 52 and 58. Alternatively, antibodies are know and can be adapted to detect the presence of specific proteins such as the p16 and Ki67 proteins in a sample. In this embodiment, the sample is first assayed with the HPV probe or the antibody probe to identify particular cells. The labeled cells are then assessed as to the chromosomal status using a probe panel of the invention. The HPV or antibody step can be performed simultaneously or sequentially with the chromosomal probe panel.

The screening test can be incorporated into the routine care of women, e.g., as an adjunct to evaluation of routine Pap smears. The methods described here can also be used to adjust treatment strategies for women. As a more reliable test than the conventional tests, e.g., Pap tests, patients can be directed more reliably to the invasive remediation (removal of the transformation zone of the patient's cervix) as necessary. Patients testing negative for high grade dysplasia by the test methodology can be spared this invasive procedure more reliably.

Probe Selection Methods

The selection of individual probes and probe sets for use with the invention can be performed using the principles described in the examples. Each probe selected for a probe set should have the ability on its own to discriminate between high and low grade dysplastic cells. Probes with high discrimination ability are preferred. The discrimination analysis described herein comprises calculating the sensitivity and specificity of each probe individually for identifying high and low grade dysplasia. Various cutoff values of cell percentages for targets gained and lost are employed. The primary metric for combined sensitivity and specificity will be a quantity called 'vector', which is defined as the magnitude of the vector drawn between the points on a sensitivity versus specificity plot representing the ideal (sensitivity=specificity=100) and the measured sensitivity and specificity of the particular probe or probe set, as measured in a cohort of abnormal and normal samples. As described in Example 2, the vector value ranges from 0 for the ideal case to 141.4 for the worst case. Statistical analyses can also be used to compare means and standard deviations between high and low grade dysplastic cells as described in U.S. patent application Ser. No. 10/081,393 by Morrison, et al. filed Feb. 20, 2002, which is incorporated herein by reference.

For multiple probes sets, each probe should be selected to complement the other probes in the set. That is, each probe should identify additional high grade dysplasia markers that the other probe(s) fail to identify. One method for identifying the best complementing set of probes is to take the probe with the lowest vector value, remove the group of tumor specimens it identified from the full set of tumor specimens, and then determine the probe with lowest vector value on the remaining tumor specimens. This process can be continued as necessary to obtain a complete probe set. The approach described here of generating all possible probe combinations, and calculating the sensitivity and specificity of each, predicts the performance of all possible probe sets and allows selection of the minimal probe set with the highest performance characteristics. Also, a variety of combinations with similarly high performance characteristics is obtained. Considering the possible errors due to the finite number of specimens tested, several of the high ranking probe combinations can be compared based on other practical characteristics such as relevance to disease prognosis or difficulty in making the probe.

However, regardless of the measured ability to complement other probes, each probe must preferably identify a statistically different percentage of test positive cells between the high and low grade adjacent specimen sets. If this condition is not met, then a probe might be selected erroneously based on apparent complementation. Moreover, data from combinations of fewer probes is more reliable than data from combinations of more probes, e.g., data from combinations of two probes is more reliable than data from combinations of three probes. This results from the reduced ability to make correlations between greater numbers of probes with the finite number of specimens tested.

The dependence of probe and probe combination performance as a function of cutoff value must also be considered. "Cutoff value" can refer to the number or percentage of cells in a population that must have gains or losses for the sample to be considered positive. Therefore, a sample can be considered positive or negative depending upon whether the number (or percentage) of cells in the specimen is above the cutoff value or equal to or less than the cutoff value, respectively. In general, the combined specificity and sensitivity of probes is better at low cutoff values. However, when the high grade dysplasia cells are distributed within a matrix containing many normal and low grade cells, such as from a cervical smear, probes performing best at high cutoffs are more likely to be detected. This is because good performance at high cutoffs indicates a higher prevalence of cells containing the abnormality. Examples of cutoff values that can be used in the determinations include about 5, 25, 50, 100 and 250 cells or 5%, 10%, 15%, 20%, 25%, 30%, 35%, 40%, 50% and 60% of cells in the sample population. In the preferred assay combining identification of HPV infected cells and determination of chromosomal abnormalities present in the HPV infected cells, a cutoff value of three (3) positive cells is preferred.

Measurement of gain of a target chromosome or chromosome region is preferred over measurement of a target chromosome or chromosome region loss, because overlapping targets or poor/failed hybridization to some cells can falsely suggest loss. Locus-specific or chromosomal arm probes designed to detect deletions are also generally smaller than locus-specific or chromosomal arm probes designed to detect gains since the deletion probes must not extend beyond the minimally deleted region. If too much of the "deletion probe" extends beyond the deleted sequence, enough signal may be produced in the assay to be falsely counted. Since "deletion probes" are usually kept small their signals are not as intense as signals for targets typically gained. This in turn makes it more likely that real signals from targets being monitored for deletion may be miscounted. Likewise, repetitive sequence probes, like some chromosome enumeration probes used here are preferable to single locus probes because they usually provide brighter signals and hybridize faster than locus specific probes. On the other hand, repetitive sequence probes are more sensitive to polymorphisms than locus specific probes.

A probe or combination of probes used with the present invention preferably provides an improvement over conventional methods such as cytology. Useful probes or probe combinations of the invention identify at least about 70% and preferably above about 85% of samples with high grade dysplasia and carcinoma (sensitivity). Similarly, useful probes or probe combinations identify as negative by test at least about 80% and preferably above about 95% of negative samples (specificity).

The invention is further described in the following examples, which are not intended to limit the scope of the invention described in the claims.

Examples

1. Initial Probe Selection. Thirty-five chromosomal regions, identified in Table 1 below, known to show some level of amplification or deletion in cervical cancer or dysplasia were selected for evaluation. The colors in Table 1 refer to the fluorescent label used for each of these probes.

TABLE 1

Probes and Gene Target Locations Used for Probe Selection.

| Set | Gold | Red | Green | Aqua | Orange |
|---|---|---|---|---|---|
| 1 | | | 1q41 | CEP 15 | 1p31 |
| | | | TGFb2 | Sat. III | D1S500 |
| 2 | 2q33-q34 | 2q24 | 2p24* | CEP 6 | |
| | HER-4 | TBR1 | MYCN | Alpha sat. | |
| 3 | 3p14 | 3p21-p23 | 3q26 | CEP 7 | |
| | FHIT | MLH | TERC | Alpha sat. | |
| 4 | 4p15.3 | | 4p16.3* | CEP 12 | |
| | DDX15 | | Wolf-Hirsch | Alpha sat. | |
| 5 | 5p13 | | 5p15.2 | CEP X | |
| | DAB2 | | D5S2064 | Alpha sat. | |
| 6 | | | 6q16.3-q21 | CEP 16 | 6p21.2 |
| | | | D6S268 | Sat. II | PIM1 |
| 11 | 11q13* | 11p15.5 | 11q23* | CEP 10 | |
| | CCND1 | HRAS | MLL | Alpha sat. | |
| CEP | CEP 11 | CEP 8 | CEP 1 | CEP 17 | |
| | Alpha sat. | Alpha sat. | Sat. II/III | Alpha sat. | |
| X | | | Xq12* | CEP 18 | Xp22.3* |
| | | | Androgen receptor | Alpha sat. | STS |
| Mixed | 8q24* | 20q13.2- | 7p12* | CEP 9 | |
| set | MYC | q13.3 STK6 | EGFR | Alpha sat. | |

Thirteen of these regions were detected using chromosome enumeration probes (CEP® probes in Table 1)) targeting repetitive centromeric sequences. Twelve of the CEP® probes used are commercially available from Vysis, Inc. (Downers Grove, Ill.). The other twenty-two regions were detected with locus specific probes targeting unique sequences within amplified or deleted chromosomal regions.

Seven of these locus specific probes used are commercially available, labeled with SpectrumOrange™ label, from Vysis, Inc. (marked with an asterisk in Table 1.) The commercial STS probe was used. For the other six probes, the same starting DNA material as used to make the commercially available probes was used. Instead of the SpectrumOrange label, the starting DNA was transaminated and then chemically labeled using 5-(and -6)-carboxyrhodamine 6G, succinimidyl ester (molecular Probes) for the c-myc and CCND1 probes, and fluorescin succinimidyl ester for the other four. The transamination and labeling process used is described in Bittner et al., U.S. Pat. No. 5,491,224, incorporated herein by reference. The CEP 11 probe labeled in gold was produced using the starting DNA material of the commercially available CEP 11 probe from Vysis, Inc., and using the same procedure as for the c-myc probe.

The remaining 14 probes were produced from BAC clones sourced as shown in Table 2.

TABLE 2

Experimental probe details.

| Probe location | Probe name | BAC clone Identification | Size of the human insert | Probe Source |
|---|---|---|---|---|
| 2q33-q34 | HER-4 | RP11 384-k20 | 156 kb | Research Genetics |
| 3p14 | FHIT | CTB-1-012 | 138 kb | Genome Systems |
| 4p15.3 | DDX15 | RP11 192p23 | 171 kb | Research Genetics |
| 2q24 | TBR1 | RP11 334e15 | 184 kb | Research Genetics |
| 3p21-p23 | MLH1 | RP11 491d6 | 102 kb | Research Genetics |
| 11p15.5 | HRAS | GS1 137c7 | 138 kb | Genome Systems |

TABLE 2-continued

Experimental probe details.

| Probe location | Probe name | BAC clone Identification | Size of the human insert | Probe Source |
|---|---|---|---|---|
| 20q13.2-q13.3 | STK6 | GS1 32i19 | 145 kb | Genome Systems |
| 1q41 | TGFB2 | RP11 224o19 | 177 kb | Research Genetics |
| 1p31 | D1S500 | RP11574n2 | 164 kb | Research Genetics |
| 6p21.2 | PIM1 | RP3 355m6 | 134 kb | Research Genetics |
| 5p13 | DAB2 | CTD-2006d4 | 127 kb | Research Genetics |

TABLE 2-continued

Experimental probe details.

| Probe location | Probe name | BAC clone Identification | Size of the human insert | Probe Source |
|---|---|---|---|---|
| 3q26 | TERC: Clone 300H Clone 300I Clone 300K Clone 300L | 4 clones: RP11 3k16 RP11 362k14 RP11 641d5 RP11 816j6 | 490 kb total contig size made up of four individual clones 200 kb 125 kb 128 kb 48 kb | All clones from Research Genetics |
| 6q16.3-q21 | D6S268 | RP1-67a8 | 155 kb | Research Genetics |
| 11q23 | MLL | 415 024 | 120 kb | Genome Systems |
| 5p.15.2 | D5S2064 | RP1-144E22 | 125.5 kb | Research Genetics |

The HER-4, FHIT, DDX15 and DAB2 probes were also produced using the same method as the c-myc probe. The remaining unique sequence probes were all produced using the nick translation method described in Morrison 2002, Id. at p. 27-30, and the labeled nucleotides Spectrum Orange dUTP, Spectru Red dUTP or Spectrum Green dUTP (all Vysis, Inc.).

The labeled probes were then separated into sets of three or four probes each for evaluation as indicated in Table 1. The probe sets were made up of the individual probes, COT1 DNA (Invitrogen), human placental DNA (Signa), and LSI/WCP Hybridization Buffer (Vysis, Inc.). 10 µl of each of the probe sets were hybridized to ten samples each of cervical biopsy samples. The probe sets each typically contained about 0.5 µg COT1 DNA and 2 µg human placental DNA. The probe set hybridization mixes also contained 50 nanograms of Spect Aqua labeled human placental DNA to provide a background staining of the nuclei in the sample, as described in U.S. Pat. No. 5,789,161, Morrison et al., incorporated herein by reference. CIN I, CIN II-III and invasive cervical squamous carcinoma (CA) samples were obtained from the Cooperative Human Tissue Network (CHTN) supported by the National Cancer Institute. The samples were prepared for hybridization and hybridized with the probe sets as follows. Paraffin embedded tissue sections were placed in xylene solution for 5 min. This procedure was repeated 3 times. Slides were then washed in 100% ethanol twice for 1 min each wash. Slides were then soaked for 15 min in 45%/0.3% peroxide solution, rinsed in water and incubated for 10 min in Pretreatment solution. After rinsing, slides were incubated with a proteinase, e.g., proteinase K or pepsin, for 5-30 min to digest excess proteins and make the DNA more accessible. The slides were then dehydrated in ethanol series, air dried and hybridized with DNA probes usually overnight at 37° C. After hybridization, unspecific probes were washed out in post-hybridization wash solutions such as for example, wash for 2 minutes in 73±1° C. 2×SSC/0.3% NP40. Slides were then washed in a second wash solution such as 2×SSC/0.1% NP40. A DAPI DNA stain was then applied to the slides to facilitate sample evaluation.

The procedure permitted all probes to hybridize to the samples. The majority of probes showed good signal intensity relative to background. The epithelial layers of the biopsy samples were evaluated under a fluorescence microscope to identify any cells that showed amplification (more than two signals) or deletion (less than two signals) of the DNA target. Gains were recorded for each sample that showed amplification in five or more cells for a particular probe; losses were recorded for each sample that showed a deletion in five or more cells. Samples showing neither gains nor losses were considered disomic.

The sensitivity, i.e., the percentage of samples showing the condition tested, of each probe for CIN I, CIN II-III and invasive carcinoma was determined for gains, losses and disomies. Losses were found to occur very infrequently in CIN II-III samples and so were not generally useful as markers for CIN II-III and invasive carcinoma. Probes were further assessed for their ability to show maximum frequency of gains for CIN II-III and minimum frequency of gains for CIN I. The results are presented in Table 3. Probes for the targets 8q24, 20q13, 3p21, 3q26, 1p31, Xp22 and CEP 15 were considered the most informative and were selected for further evaluation. The 3 p14 probe showed significant loss in the CIN II-III and invasive carcinoma samples. The ratio of the relative gain of 3q26 to 3 p14 was also evaluated as a measure of the relative gain of the q arm of chromosome 3 to its p arm.

TABLE 3

Sensitivity of Probes for Detecting Gains, Losses and Disomies in Cervical Specimens.

| | Gain | | | Loss | | | Disomy | | |
|---|---|---|---|---|---|---|---|---|---|
| Probe | CIN I | CIN II-III | CA | CIN I | CIN II-III | CA | CIN I | CIN II-III | CA |
| 8q24 | 0 | 80 | 100 | 0 | 0 | 0 | 100 | 20 | 0 |
| Xp22 | 0 | 70 | 75 | 19 | 0 | 5 | 81 | 30 | 20 |
| CEP 15 | 0 | 70 | 90 | 0 | 0 | 0 | 100 | 30 | 10 |
| 20q13 | 10 | 80 | 90 | 0 | 0 | 0 | 90 | 20 | 10 |
| 1p31 | 10 | 70 | 80 | 0 | 0 | 0 | 90 | 30 | 20 |
| 3p21 | 13 | 85 | 55 | 6 | 0 | 18 | 81 | 15 | 27 |
| CEP 10 | 15 | 70 | 100 | 10 | 0 | 0 | 75 | 30 | 0 |
| 3q26 | 25 | 80 | 100 | 5 | 0 | 0 | 70 | 20 | 0 |
| 5p13 | 30 | 80 | 100 | 5 | 0 | 0 | 65 | 20 | 0 |
| CEP 8 | 30 | 78 | 100 | 5 | 0 | 0 | 65 | 22 | 0 |
| 5p15 | 40 | 80 | 100 | 5 | 0 | 0 | 55 | 20 | 0 |
| CEP X | 50 | 75 | 100 | 5 | 0 | 0 | 45 | 25 | 0 |
| 2p24 | 20 | 67 | 90 | 0 | 0 | 0 | 80 | 33 | 10 |
| Xq12 | 14 | 60 | 95 | 14 | 0 | 5 | 74 | 40 | 0 |
| CEP 7 | 25 | 60 | 90 | 5 | 0 | 10 | 70 | 40 | 0 |
| CEP 18 | 12 | 60 | 90 | 0 | 0 | 0 | 88 | 40 | 10 |
| CEP 16 | 20 | 60 | 100 | 0 | 0 | 0 | 80 | 40 | 0 |
| 7p12 | 10 | 60 | 90 | 0 | 0 | 10 | 90 | 40 | 0 |
| 3p14 | 10 | 60 | 9 | 10 | 20 | 82 | 80 | 20 | 9 |

TABLE 3-continued

Sensitivity of Probes for Detecting Gains, Losses and Disomies in Cervical Specimens.

| | | | | | | | | | |
|---|---|---|---|---|---|---|---|---|---|
| 1q41 | 10 | 60 | 90 | 0 | 0 | 10 | 90 | 40 | 0 |
| 11q13 | 25 | 60 | 85 | 0 | 0 | 0 | 75 | 40 | 15 |
| CEP 12 | 10 | 55 | 100 | 5 | 0 | 0 | 85 | 45 | 0 |
| CEP 6 | 10 | 50 | 100 | 10 | 0 | 0 | 80 | 50 | 0 |
| 4p16 | 30 | 50 | 80 | 0 | 0 | 0 | 70 | 50 | 20 |
| 4p15 | 20 | 50 | 70 | 0 | 0 | 0 | 80 | 50 | 30 |
| 2q33 | 12 | 50 | 50 | 12 | 12 | 15 | 76 | 38 | 35 |
| 11p15 | 15 | 50 | 90 | 0 | 0 | 0 | 85 | 50 | 10 |
| CEP 11 | 20 | 45 | 100 | 5 | 0 | 0 | 75 | 55 | 0 |
| CEP 9 | 0 | 44 | 100 | 5 | 0 | 0 | 95 | 56 | 0 |
| CEP 17 | 10 | 40 | 100 | 5 | 0 | 0 | 85 | 60 | 0 |
| 6q16-21 | 10 | 40 | 73 | 0 | 10 | 0 | 90 | 50 | 27 |
| CEP 1 | 13 | 33 | 100 | 6 | 0 | 0 | 81 | 57 | 0 |

| | Gain | Loss | Disomy | | Gain | Loss | Disomy | | Gain |
|---|---|---|---|---|---|---|---|---|---|
| 2q23 | 20 | 30 | 80 | 0 | 10 | 0 | 80 | 60 | 20 |
| 11q23 | 45 | 30 | 80 | 0 | 0 | 0 | 55 | 70 | 20 |
| 6p21 | 0 | 10 | 77 | 5 | 10 | 0 | 95 | 80 | 23 |

2. Discriminate Analysis of In Situ Hybridization Data and Selection of Probe Sets. Additional paraffin embedded biopsy samples classed as normal (WNL), CIN I, CIN II, CIN III and Squamous cell carcinoma (CA) were obtained from the University of Texas Southwestern Medical Center, Dallas, Tex. (Dr. Raheela Ashfaq). The samples were prepared and hybridized to two sets of probes (CEP 15, 8q24, Xp22 and 20q13; and CEP 3, 3q26, 3q14 and 3p21) as before. Six of the probes used—8q24, Xp22, CEP 15, 20q13, 3p21 and 3q26—were taken from the preferred probes identified in Example 1. Two others—CEP 3 and 3p14—were compared with probes to 3p21 and 3q26 to better assess the relationship of chromosome 3 in the progression to cervical cancer.

The ability of individual probes and certain probe combinations to discriminate between high and low grade dysplasia in cervical cells was evaluated by determining the number of specimens correctly identified by each probe or probe set. A cutoff number of five cells with gains or losses was used to evaluate samples. A sample was called positive or negative for high grade dysplasia or carcinoma depending upon whether the number of cells in the sample was above the cutoff value or equal to or less than the cutoff value, respectively. The accuracies of identifying the positive samples (sensitivity) and negative samples (specificity) were then used to select the best probes and probe combinations. Table 3a lists the specificity and sensitivity of gain and loss for certain probe targets.

TABLE 3a

Sensitivity and specificity measurements relative to sample grades.

| Probe | Specificity WNL | Specificity CIN I | Specificity WNL + CIN I | Sensitivity CIN II | Sensitivity CIN III | Sensitivity CA | Sensitivity CIN II + CIN III + CA |
|---|---|---|---|---|---|---|---|
| CEP15 | 100.00 | 89.47 | 94.74 | 48.15 | 60.00 | 57.89 | 55.35 |
| 8q24 | 95.24 | 73.68 | 84.46 | 96.30 | 95.00 | 100.00 | 97.10 |
| Xp22 | 100.00 | 89.47 | 94.74 | 59.26 | 70.00 | 94.74 | 74.67 |
| 20q13 | 100.00 | 78.95 | 89.48 | 66.67 | 70.00 | 100 | 78.89 |
| CEP3 | 100.00 | 84.21 | 92.11 | 55.56 | 70.00 | 68.42 | 64.66 |
| 3q26 | 100.00 | 73.68 | 86.84 | 77.78 | 90.00 | 100.00 | 89.26 |
| 3p14 | 100.00 | 78.95 | 89.47 | 33.33 | 60.00 | 15.79 | 36.37 |
| 3p21 | 100.00 | 84.21 | 92.11 | 37.04 | 65.00 | 21.05 | 41.03 |
| Gain 3q26 & Loss 3p14 | 100.00 | 100.00 | 100.00 | 7.41 | 15.00 | 78.95 | 33.79 |
| Ratio 3q26/CEP3 > 1 | 100.00 | 89.47 | 94.74 | 29.63 | 70.00 | 84.21 | 61.28 |
| Ratio 3q26/3p14 > 1 | 95.24 | 84.21 | 89.73 | 66.67 | 80.00 | 94.74 | 80.47 |
| Loss: 3p14 < 1 | 95.24 | 100 | 97.62 | 29.63 | 15.00 | 89.47 | 44.70 |

The ability to discriminate between cellular types depends on the overall specificity and sensitivity. Good discrimination requires good specificity and sensitivity. Table 3b presents results for a combined measure of specificity and sensitivity designated "vector". Vector is calculated as $$\text{Vector}=[(100-\text{specificity})^2+(100-\text{sensitivity})^2]^{1/2}$$

Specificity and sensitivity are defined as percentages and range from 100% (perfect) to 0% for no specificity (or sensitivity) at all. Hence, vector values range from 0 for perfect specificity and sensitivity to 141 for zero specificity and sensitivity.

Table 3b is sorted by increasing vector value for each sample category. Individual probes showing a high ability to discriminate (low vector value) include 3q26, 8q24 and CEP 3. Other probes showing a useful ability to discriminate high grade dysplasia and carcinoma from low grade dysplasia are 20q13, Xp22, CEP 15 and 3p21. Vectors determined for probe ratios such as 3q26/CEP (determined to be >1) and 3q26/3 p14 (determined to be >1) can also be useful. Other methods for evaluating and selecting probes using discriminate and combinatorial analytical techniques are described in U.S. Ser. No. 10/081,393 by Morrison, et al., filed Feb. 20, 2002, which is incorporated herein by reference.

TABLE 3b

Vector value for sample grades.

| Probe/Vector | CIN I vs CIN II | WNL + CIN I vs CIN II | (WNL + CIN I) vs (CIN II + CIN III) |
|---|---|---|---|
| 3q26 | 27.00 | 17.75 | 13.50 |
| 8q24 | 28.07 | 16.76 | 16.87 |
| CEP3 | 35.55 | 33.82 | 25.69 |
| 20q13 | 41.11 | 36.34 | 33.49 |
| Xp22 | 43.73 | 42.66 | 35.88 |
| CEP 15 | 51.22 | 50.31 | 46.76 |
| 3p21 | 54.59 | 53.63 | 39.59 |
| Ratio 3q26/CEP 3 > 1 | 54.59 | 53.63 | 31.36 |
| Ratio 3q26/3p14 > 1 | 54.59 | 53.63 | 31.36 |
| 3p14 | 62.53 | 60.64 | 47.47 |
| Gain 3q26&Loss 3p14 | 93.30 | 93.30 | 88.30 |
| Loss: 3p14 < 1 | 93.30 | 93.30 | 88.30 |

Based on results from discriminate analysis and probe complementarity as described above, preferred probes for use in distinguishing high from low grade dysplasia in cervical samples include probes to the loci 3q26 and 8q24 and the CEP 3. Sets of probes comprising the probes 3q26 and 8q24; 3q26, 8q24, Xp22, and CEP 15; 8q24, 20q13, Xp22 and CEP 15; and 3p21, 3p14, 3q26 and CEP 3 are particularly preferred.

3. Combined HPV and Chromosomal Gain Assay. A fluorescence in situ hybridization assay to detect the presence of BPV infection and chromosomal gains in the same cell(s) was developed and tested.

HPV Plasmids and Probe Composition

Plasmids containing the full coding sequence of HPV-16, HPV-18, HPV-30, BPV-45, HPV-51 and HPV-58 were used to generate biotin labeled DNA probes by nick translation using a convention protocol. HPV plasmids were obtained from the following sources: HPV-16 and HPV-18 were purchased from the American Type Tissue Collection (ATTC), BPV-30 and HPV-45 were obtained from Dr. Ethel-Michele de Villiers (DKFZ, Germany), and HPV-51 and BPV-58 plasmids were obtained from Klara Abravaya (Abbott Laboratories). The original sources for the HPV-51 and HPV-58 plasmids are Dr. Saul Silverstein (Columbia University) and Dr. Toshihiko Matsukura (Japan), respectively.

These six HPV probes were combined with locus specific 8q24 (cmyc) and 3q26 (TERC) probes and the centromeric probe CEP-8. The locus specific 8q24 and 3q26 probes used were those described above in Example 1., except that the 8q24 probe was labeled in Spectrum Red and the 3q26 probe was labeled in Spectrum Yellow using the method described in Example 1.

The composition of the probe mix is: 1X LSI buffer, 2×SSC, 7.5 µg/m of Spectrum Red cmyc (8q24), 10.0 µg/ml of Spectrum Yellow TERC (3q26), 2.5 µg/ml of Spectrum Aqua CEP-8, 2.5 µg/ml each of Biotin labeled HPV-16, HPV-18, HPV-30, HPV-45, HPV-51 and BPV-58, 200 µg/ml of human placenta DNA, and 100 µg/ml of Cot-1 DNA.

Sample Preparation and Assay Protocol

Residual Thin-Prep preserved cervical specimens were obtained from Mayo Clinic. Thin-Prep slides from the preserved cervical specimens were prepared following the manufacturer's instructions (Cytyc). The samples were prepared for hybridization as follows. Thin-Prep slides were soaked in 2×SSC at 73° C. for 2 minutes, followed by incubation in pepsin (0.5 mg/ml in 10 mM HCL) at 37° C. for 110 minutes. The slides were then washed in 1×PBS at room temperature for 5 minutes, fixed in 1% NBF (NBF-neutral buffer formalin) room temperature for five minutes, and rinsed in 1×PBS at room temperature for 5 minutes. After rinsing, the slides were dehydrated in ethanol series, air dried and hybridized with the combined HPV and chromosomal probe mix overnight at 37° C.

After hybridization, excess probes were washed in post-hybridization wash consisting of 2×SSC/0.3% NP-40 for 2 minutes at 48° C. and then 2×SSC/0.1% NP-40 for 1 minute at room temperature.

Detection of the Biotin labeled HPV probes was performed using the Alexa Fluorm 488 Tyramide signal amplification kit (Molecular Probes) following the manufacturer's directions. Briefly, endogenous peroxidase activity was blocked by incubation in 3% $H_2O_2$ for 30 minutes at room temperature and slides were washed in 1×PBS for 5 minutes at room temperature. Slides were then incubated with 1% Blocking Reagent in PBS at 37° C. for 25 minutes followed by Streptavidin-HRP at 37° C. for 25 minutes. After washing the slides 3 times in 1×PBS, the biotin labeled BPV probe/Streptavidin-HRP complex was visualized by incubation with Alexa Fluor 488 labeled tyramide for 10ζ at room temperature. The slides were then washed in 1×PBS, the nuclear counterstain DAPI was applied and slides were coverslipped.

Hybridized slides are analyzed under a fluorescence microscope. HPV probe is visualized using the green filter and the staining could appear as a diffuse staining throughout the cell nucleus, punctate staining or mixed staining (punctuate and diffuse). Probe for Spectrum Yellow 3q26 is detected using a gold filter, Spectrum Red 8q24 is detected using a red filter, and Spectrum Aqua CEP8 is detected using an aqua filter. All filters used are commercially available from Vysis, Inc., Downers Grove, Ill.

HPV-Chromosomal Gain Assay Results

Residual Thin-Prep preserved cervical specimens were obtained from Mayo Clinic. Fifty-seven specimens diagnosed with LSIL or HSIL cytology were analyzed. After hybridization and washing as described above, the slides were evaluated using fluorescence microscopy for the presence of HPV and chromosomal gains. Results were correlated with available histology and clinical follow up. Slide analysis was performed as follow: (1) The whole surface area of the slide was analyzed using 40× magnification to identify HPV positive cells, (2) For each positive cell the BPV pattern (diffuse, punctate, or mix) and the chromosomal counts for each probe were recorded, (3) In addition, chromosomal gains were analyzed independent of the HPV status of the cell. Cells with 3 or more signals for the MYC or TERC probe were recorded. The results are set out in Tables 4 and 5.

TABLE 4

Characteristics of the cytological groups of specimens

| MEASURED FEATURE | LSIL GROUP | HSIL GROUP |
|---|---|---|
| Number of samples per group | 30 | 27 |
| Number of HPV Positive samples | 19/30 = 63% | 22/27 = 82% |

TABLE 4-continued

Characteristics of the cytological groups of specimens

| MEASURED FEATURE | LSIL GROUP | HSIL GROUP |
|---|---|---|
| Number of samples with concurrent biopsy n = 23 | 11/30 = 36% | 12/27 = 44% |
| Number of samples with concurrent CIN2+ biopsy n = 10 | 1 | 9 |
| Number of samples with concurrent CIN1 biopsy n = 11 | 8 | 3 |
| Number of samples with concurrent Negative/Benign biopsy n = 2 | 2 | 0 |

TABLE 5

Data Analysis for CIN2+ and CIN1 Groups
SENSITIVITY AND THE SPECIFICITY OF CERVICAL TEST USING
DIFFERENT MOLECULAR MARKERS

| Criteria for Test Positivity | SENSITIVITY (CIN2+ specimens n = 10) | SPECIFICITY (CIN1 specimens n = 11) |
|---|---|---|
| FISH TEST - 30 abn cells | 5/10 = 50% | 8/11 = 73% |
| FISH TEST - 20 abn cells | 7/10 = 70% | 5/11 = 45% |
| HPV TEST - 30 pos cells | 9/10 = 90% | 10/11 = 91% |
| HPV TEST - 20 pos cells | 10/10 = 100% | 8/11 = 73% |
| HPV/FISH OVERLAP TEST - 3 HPV+/FISH+ cells | 9/10 = 90% | 8/11 = 73% |
| HPV/FISH OVERLAP TEST - 1 HPV+/FISH+ cells | 9/10 = 90% | 5/11 = 45% |

As shown in Table 5, the combined HPV chromosomal abnormality assay was able to identify high grade dysplasia at high sensitivity of 90% using a cutoff value of three positive cells, while retaining acceptable specificity.

Other Embodiments

While the invention had been described in conjunction with the foregoing detailed description, it is to be understood that the foregoing description is intended to illustrate and not limit the scope of the invention. Other aspects, advantages and modification of the invention are within the scope of the claims set forth below.

We claim:

1. A method for screening for cervical high grade squamous intraepithelial lesion (HSIL) in a human subject, the method comprising:
   a. obtaining a cervical sample containing a plurality of cervical cells from the subject;
   b. contacting the sample with a set of two or more chromosomal probes comprising chromosomal probes specific for loci 8q24 and 20q13 able to detect HSIL under conditions sufficient to enable hybridization of the probes to any chromosomes in the sample; and,
   c. detecting the hybridization pattern of the chromosomal probes to the plurality of cells in the sample, wherein said hybridization pattern is indicative of amplification of loci 20q13 and 8q24 and correlating said amplification of loci 20q13 and 8q24 with the presence of cervical HSIL in said subject.

2. The method of claim 1, wherein the sample comprises a biopsy.

3. The method of claim 1, wherein the sample comprises a cervical smear or cervical scrape sample.

4. The method of claim 1, wherein the chromosomal probes are fluorescently labeled.

5. The method of claim 1, wherein the set of two or more chromosomal probes additionally comprises probes specific for 3q26, Xp22 and CEP 15.

6. The method of claim 1, wherein the set of two or more chromosomal probes additionally comprises probes specific for 3p21, 3p14 and CEP 3.

7. The method of claim 1 wherein cells from the cervical sample are prescreened for a marker associated with risk for cancer.

8. The method of claim 1 wherein cells from the cervical sample are prescreened for infection by HPV.

9. The method of claim 8 wherein the sample is screened for infection by one or more of the high risk HPV types selected from the group consisting of 16, 18, 31, 33, 35, 52 and 58.

10. The method of claim 1 wherein cells from the cervical sample are prescreened for the presence of a cell cycle protein or a cell proliferation marker.

11. The method of claim 10 wherein the cell cycle protein is p16 or Cyclin E.

12. The method of claim 10 wherein the cell proliferation marker is the protein Ki67 or the protein PCNA.

13. A method for screening for cervical HSIL in a human subject, the method comprising:
   a. obtaining a cervical sample containing a plurality of cervical cells from the subject;
   b. contacting the sample with a set of two or more chromosomal probes comprising chromosomal probes specific for loci 8q24 and 20q13 able to detect HSIL and a mixture of HPV probes under conditions sufficient to enable hybridization of the probes to any chromosomes in the sample and sufficient to enable detection of any HPV infected cells present in the sample;
   c. detecting the presence of HPV infected cells in the sample;
   d. determining hybridization pattern of the chromosomal probes in the HPV infected cells in the plurality of cervical cells in the sample, wherein said hybridization pattern is indicative of amplification of loci 20q13 and 8q24 and correlating said amplification of loci 20q13 and 8q24 with the presence of cervical HSIL.

14. The method of claim 13 wherein the mixture of HPV probes consists of probes substantially complementary to full coding sequence for each of HPV-16, HPV-18, HPV-30 and HPV-58.

15. The method of claim 13, wherein the set of two or more chromosomal probes additionally comprises probes specific for 3q26, Xp22 and CEP 15.

16. The method of claim 13, wherein the set of two or more chromosomal probes additionally comprises probes specific for 3p21, 3p14 and CEP 3.

17. The method of claim 15 wherein the set of two or more chromosomal probes comprises probes to the TERC locus at 3q26, the cmyc locus at 8q24 and the centromere of chromosome 8.

18. The method of claim 14 wherein hybridization conditions are sufficient to detect the presence of any of HPV-31, HPV-33, HPV-35, HPV-39, HPV-52, HPV-56, HPV-58, HPV-59, HPV-26, HPV-53, and HPV-66.

19. The method of claim 14, wherein each of the HPV probes in the mixture comprise a biotin label.

20. The method of claim 16 wherein the detecting of the presence of HPV infection and the determination of the hybridization pattern of the chromomal probes is performed using digital imaging.

21. The method of claim 16 wherein presence of a hybridization pattern indicative of the presence of cervical HSIL is identified in three or more HPV infected cells.

22. The method of claim 20 wherein presence of a hybridization pattern indicative of the presence of cervical HSIL is identified in one or more HPV infected cells.

23. The method of claim 1, wherein the sample is contacted with two to not more than four chromosomal probes.

* * * * *